United States Patent
Brown

(10) Patent No.: US 9,418,420 B2
(45) Date of Patent: Aug. 16, 2016

(54) SYSTEM AND METHOD FOR AUTOMATED DETECTION OF LUNG NODULES IN MEDICAL IMAGES

(71) Applicant: THE REGENTS OF THE UNIVERSITY OF CALIFORNIA, Oakland, CA (US)

(72) Inventor: Matthew S. Brown, Marina del Rey, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/643,791

(22) Filed: Mar. 10, 2015

(65) Prior Publication Data
US 2015/0254842 A1 Sep. 10, 2015

Related U.S. Application Data

(63) Continuation of application No. PCT/US2013/029646, filed on Mar. 7, 2013.

(60) Provisional application No. 61/700,592, filed on Sep. 13, 2012.

(51) Int. Cl.
*G06K 9/00* (2006.01)
*G06T 7/00* (2006.01)
*G06K 9/46* (2006.01)
*G06K 9/52* (2006.01)
*G06K 9/62* (2006.01)
(Continued)

(52) U.S. Cl.
CPC ............ *G06T 7/0012* (2013.01); *G06K 9/46* (2013.01); *G06K 9/52* (2013.01); *G06K 9/6267* (2013.01);
(Continued)

(58) Field of Classification Search
CPC .......... G06T 2207/10081; G06T 2207/30061; G06T 2207/30064; G06T 2207/20141; G06T 2207/2018; G06T 2207/20152; G06T 7/0081; G06T 7/0083; G06T 7/0034; G06T 7/0097; G06K 9/46; G06K 9/52; G06K 9/6267; G06K 2009/4666
USPC .......................................... 382/131
See application file for complete search history.

(56) References Cited

U.S. PATENT DOCUMENTS

2003/0167001 A1   9/2003   Allain et al.
2004/0227756 A1   11/2004  Dicken
(Continued)

OTHER PUBLICATIONS

Korean Intellectual Property Office (KIPO), International Search Report and Written Opinion, issued Jun. 19, 2013 for PCT International application No. PCT/US2013/029646, pp. 1-9, with claims searched, pp. 10-15, corresponding to U.S. Appl. No. 14/643,791.

(Continued)

*Primary Examiner* — Ali Bayat
(74) *Attorney, Agent, or Firm* — O'Banion & Ritchey LLP; John P. O'Banion

(57) ABSTRACT

A system and method for automatically segmenting a computed tomography (CT) image of a patient's lung. The method includes the steps of segmenting the CT image to acquire one or more lung regions, intensity thresholding the lung regions to generate a mask region comprising high-intensity regions corresponding to anatomical structures within the lung regions, computing a Euclidean distance map of the mask region, performing watershed segmentation of the Euclidean distance map to generate one or more sub-regions, identifying a seed point for each sub region, growing candidate regions from the seed point of each sub-region, and classifying one or more candidate regions as a lung nodule based on one or more geometric features of the candidate regions.

32 Claims, 10 Drawing Sheets

(51) Int. Cl.
*A61B 6/03* (2006.01)
*A61B 6/12* (2006.01)
*A61B 6/00* (2006.01)

(52) U.S. Cl.
CPC ............ *G06T 7/0081* (2013.01); *G06T 7/0091* (2013.01); *A61B 6/032* (2013.01); *A61B 6/12* (2013.01); *A61B 6/50* (2013.01); *A61B 6/5217* (2013.01); *G06K 2009/4666* (2013.01); *G06T 2207/10081* (2013.01); *G06T 2207/20141* (2013.01); *G06T 2207/20152* (2013.01); *G06T 2207/30064* (2013.01); *G06T 2207/30096* (2013.01)

(56) References Cited

U.S. PATENT DOCUMENTS

| | | | | |
|---|---|---|---|---|
| 2005/0286750 | A1* | 12/2005 | Dehmeshki | G06K 9/342 382/131 |
| 2006/0106299 | A1* | 5/2006 | Uchizono | G01R 33/3415 600/410 |
| 2007/0092864 | A1* | 4/2007 | Reinhardt | G06T 7/0012 435/4 |
| 2008/0002870 | A1 | 1/2008 | Farag et al. | |
| 2009/0092302 | A1* | 4/2009 | Kubota | G06T 7/0012 382/128 |
| 2010/0266173 | A1 | 10/2010 | Lorenz et al. | |
| 2010/0272341 | A1 | 10/2010 | Reeves et al. | |
| 2013/0121556 | A1* | 5/2013 | Matsumoto | A61B 6/50 382/132 |

OTHER PUBLICATIONS

Brown, Matthew S. et al., "Toward clinically usable CAD for lung cancer screening with computed tomography", Eur Radiol (2014) 24:2719-2728, European Society of Radiology, published online Jul. 24, 2014.

* cited by examiner

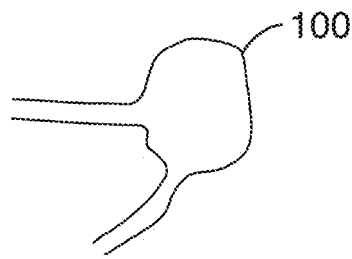 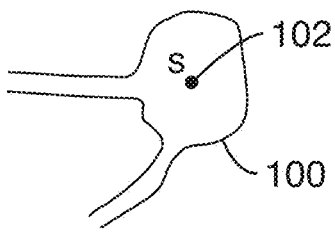
FIG. 8A    FIG. 8B
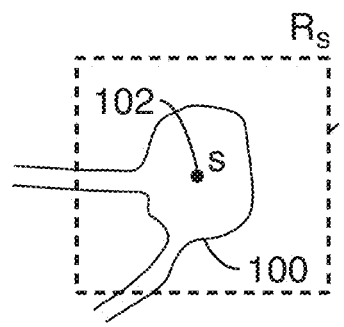 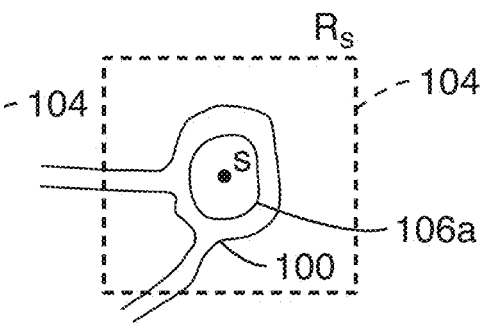
FIG. 8C    FIG. 8D
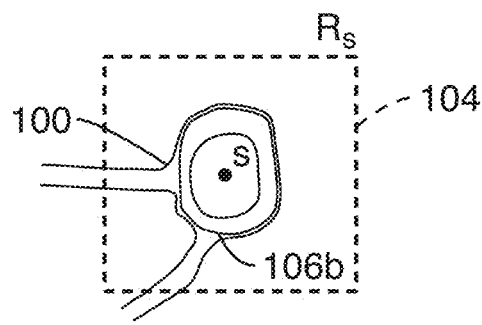
FIG. 8E

SYSTEM AND METHOD FOR AUTOMATED DETECTION OF LUNG NODULES IN MEDICAL IMAGES

CROSS-REFERENCE TO RELATED APPLICATIONS

This application is a 35 U.S.C. §111(a) continuation of PCT international application number PCT/US2013/029646 filed on Mar. 7, 2013, incorporated herein by reference in its entirety, which claims priority to, and the benefit of, U.S. provisional patent application Ser. No. 61/700,592 filed on Sep. 13, 2012, incorporated herein by reference in its entirety. Priority is claimed to each of the foregoing applications.

The above-referenced PCT international application was published as PCT International Publication No. WO 2014/042678 on Mar. 20, 2014, which publication is incorporated herein by reference in its entirety.

STATEMENT REGARDING FEDERALLY SPONSORED RESEARCH OR DEVELOPMENT

This invention was made with Government support under CA088973, awarded by the National Institutes of Health. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to computed tomography imaging, and more particularly to automated detection and measurement of lung nodules in medical images.

2. Description of Related Art

Computed Tomography (CT) imaging has been used for in vivo assessment of the location, extent, and progression of lung disease in patients. The ability to perform these analyses routinely and reliably in large patient cohorts is important to enable deployment of the methods in clinical trials and practice. However, the role of diagnostic imaging has generally been limited to visual inspection in clinical practice.

For analysis to be feasible in clinical practice, reliable automation is needed based on the size of the data sets (>400 cross-sectional images for isotropic voxel spacing). Lung cancer is the leading cause of death due to cancer. Imaging is used for detection, diagnosis, measurement, and follow-up of lung nodules.

Nodule detection is one of the more challenging visual detection tasks in medical imaging. Nodules may be difficult to detect visually on images because of low contrast, small size, or location of the nodule within an area of complicated anatomy such as the hilum. Reader fatigue, distraction, and satisfaction of search from the observation of unrelated pathology are other recognized causes of missed nodules. Thinner slices and overlapping reconstruction intervals improve the longitudinal resolution, but require large data sets (700 or more cross-sectional images) to be generated, contributing to the difficulty of interpretation and potential for missed nodules.

It has been shown that automated computer detection of lung nodules can assist a reader in more accurate and consistent detection of lung nodules [Brown 2005].

There have been numerous computer-aided detection (CAD) systems developed for lung nodules in computed tomography (CT) images [Girvin 2008]. However, CAD is not in widespread clinical use because of an inability to limit false positive detections, e.g., normal anatomy such as blood vessel or airway branches that are incorrectly detected by CAD as nodules. These false positives not only take time to rule out, but some studies suggest that radiologists can incorrectly accept false positives, which in practice would lead to unnecessary workups.

Also, most previous methods have tended to focus on solid nodules which appear brighter in images and are thus easier to detect (e.g., using a threshold above −300 HU). If a method attempts to detect faint ground glass nodules (with intensity of around −700 HU) they typically generate too many false positives to be practical.

BRIEF SUMMARY OF THE INVENTION

Accordingly, an object of the present invention is the development of algorithms to improve accuracy in detecting nodules while ruling out normal anatomic structures. The present invention incorporates automated and interactive systems for lung image analysis, in particular a Euclidean distance transformation and segmentation approach based on watersheds that maintains a low level of false positive detections even while achieving high sensitivity for solid and faint ground glass nodules.

One aspect is a lung nodule detection system that is configured to detect and report both solid and ground glass nodules, with diameter above a threshold (e.g., 4 mm) or twice the image slice thickness, whichever is larger.

Another aspect is a method that provides improved segmentation and shape characterization of high intensity regions within the lung for better differentiation between nodules that tend to be spherical, and vessels that are generally more tubular. The improved discrimination of the present invention decreases the number of false positives arising from the CAD system, while maintaining sensitivity.

A further aspect is a method for automatically segmenting a computed tomography (CT) image of a patient's lung. The method includes the steps of segmenting the CT image to acquire one or more lung regions, intensity thresholding the lung regions to generate a mask region comprising high-intensity voxels corresponding to anatomical structures within the lung regions, computing a Euclidean distance map of the mask region, performing watershed segmentation of the Euclidean distance map to generate one or more sub-regions, identifying a seed point for each sub region, growing candidate regions from the seed point of each sub-region, and classifying one or more candidate regions as a lung nodule based on one or more geometric features of the candidate regions.

Another aspect is a system for automatically segmenting a computed tomography (CT) image of a patient's lung. The system includes a processor and programming executable on the processor for segmenting the CT image to acquire one or more lung regions, intensity thresholding the lung regions to generate a mask region comprising high-intensity voxels corresponding to anatomical structures within the lung regions, computing a Euclidean distance map of the mask region, performing watershed segmentation of the Euclidean distance map to generate one or more sub-regions, identifying a seed point for each sub region, growing candidate regions from the seed point of each sub-region, and classifying one or more candidate regions as a lung nodule based on one or more geometric features of the candidate regions.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 8A through FIG. 8E are schematic representations of lung nodule distance map segmentation step of FIG. 5, with FIG. 8A showing the watershed region, FIG. 8B showing seed point generation, FIG. 8C showing region of interest generation, FIG. 8D showing a region-growing result, and FIG. 8E showing a dilation result.

DETAILED DESCRIPTION OF THE INVENTION

Figure 1:
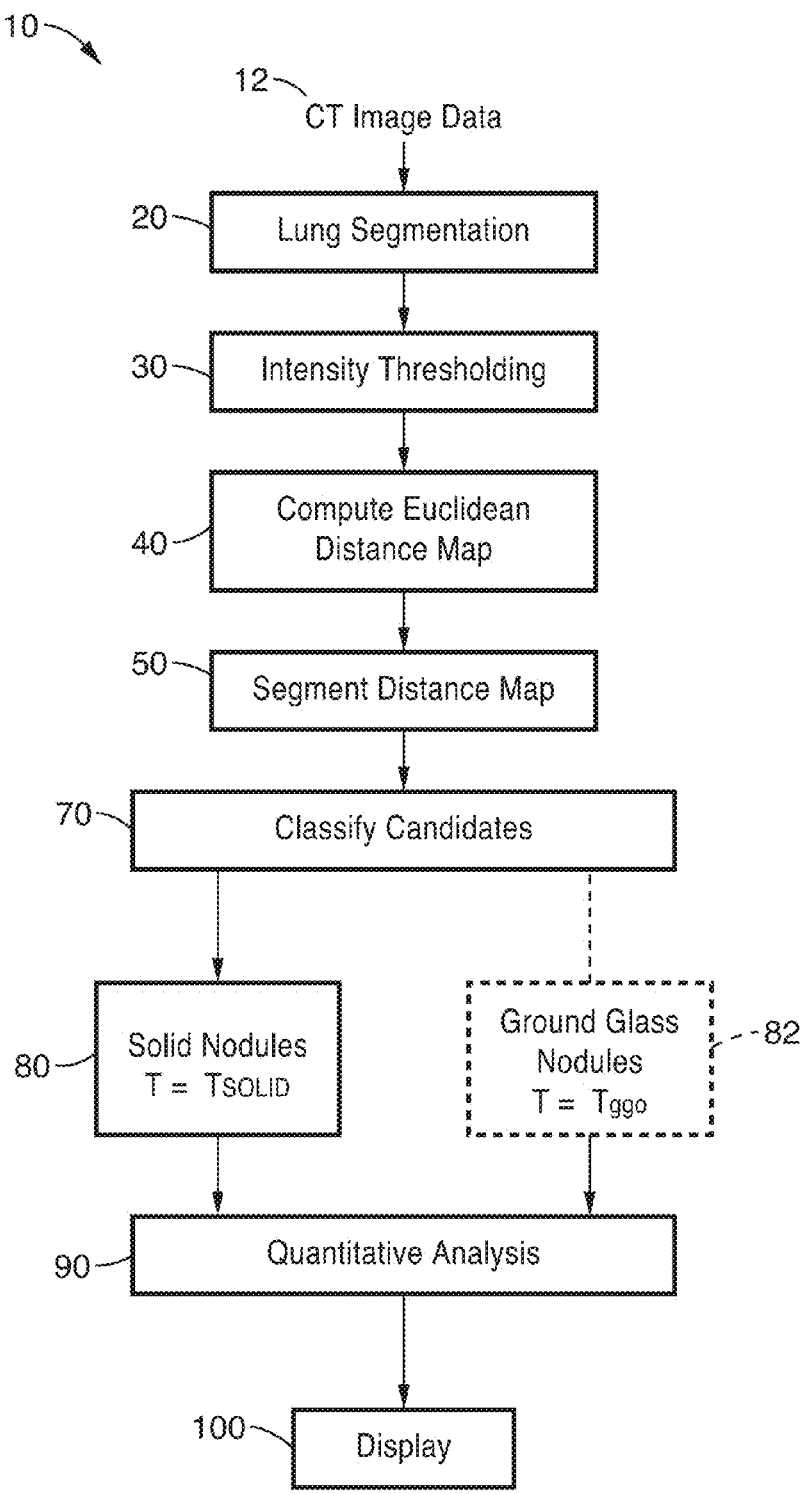
FIG. 1 illustrates an overview flow diagram of the lung nodule detection method of the present invention.

FIG. 1 illustrates an overview flow diagram of the lung nodule detection method 10 of the present invention. The scanned CT images 12 are first segmented at step 20. Next, intensity thresholding is performed is performed at step 30. This data is then used for performing Euclidean distance transformation at step 40. The distance map is then segmented at step 50. Candidates are classified at step 70. Solid nodules are detected at step 80 based on threshold $T=T_{solid}$. For detection of ground class nodules at step 82, intensity thresholding step 30, Euclidean distance transformation step 40, and distance map segmentation step 50 are repeated based on threshold $T=T_{ggo}$ (see FIG. 3, FIG. 4 and FIG. 5). At step 90, quantitative assessment may be performed for regions of interest (ROI's) identified as nodules. The detected nodules may then be displayed as overlays in step 100.

Figure 2:
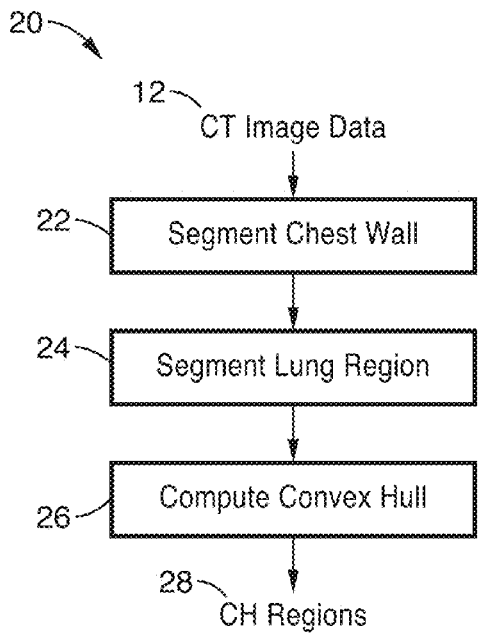
FIG. 2 is a detailed flow diagram of the lung segmentation step of FIG. 1.

FIG. 2 is a detailed flow diagram of the lung segmentation step 20 of

FIG. 1, which incorporates region-growing and morphology for segmentation followed by fuzzy logic to match image regions to anatomical structures. Lung segmentation is performed using a combination of gray-level thresholding and three-dimensional (3-D) region-growing. The processing is spatially constrained using information from an anatomical model (not shown).

First, the chest wall from CT image data 12 is segmented at step 22 by intensity-thresholding for bright voxels in the CT image and selecting the largest 3D connected component. The lung region is then segmented at step 24 by intensity-thresholding dark voxels within the chest (also selecting the largest 3D connected component). An example of this step is shown in FIG. 9B.

Finally, the convex hull of the lung regions is computed at step 26 to enclose nodules that would otherwise be excluded from the lung region to generate the segmented convex hull (CH) regions 28. FIG. 9C shows results from an exemplary CH segmentation step.

Figure 3:
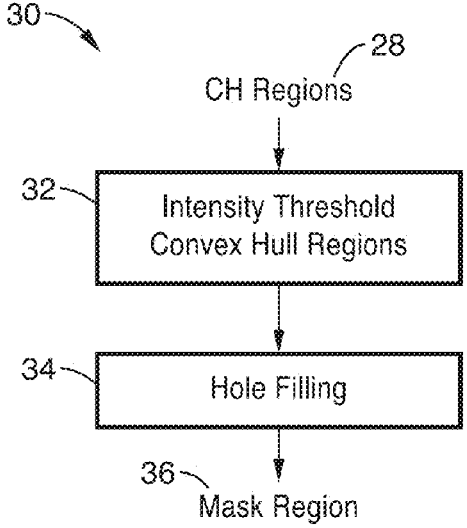
FIG. 3 is a detailed flow diagram of the intensity thresholding step of FIG. 1.

FIG. 3 is a detailed flow diagram of the intensity thresholding step 30. Within the segmented lung convex hull regions 28 generated from step 26, intensity-thresholding on the CT image 12, $I_{CT}$, is performed at step 32 to extract a region of relatively high intensity corresponding to nodules, blood vessels, airway walls, etc. It is to be noted that the thresholding performed in step 30 is performed at a lower threshold value T than that performed in segmenting step 20 for the chest wall. The threshold region $R_T$ is represented as a binary image mask according to Eq. 1, where, for a voxel v:

$$R_T(v)=1 \text{ if } I_{CT}(v) \geq T \text{ and } R_T(v)=0 \text{ otherwise.} \qquad \text{Eq. 1}$$

Next, at step 34, morphological closing and hole filling is applied to $R_T$ to generate a final mask region 36, $R_m$.

Figure 4:
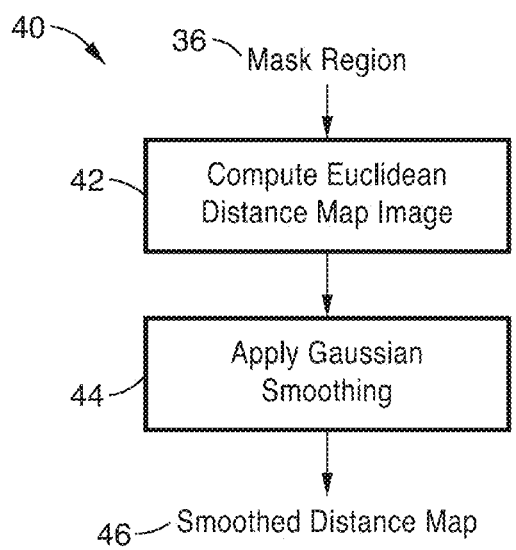
FIG. 4 is a detailed flow diagram of the Euclidean distance map estimation step of FIG. 1.

FIG. 4 is a detailed flow diagram of the Euclidean distance map estimation step 40. Using the binary image mask 36, $R_m$ from step 34, a Euclidean distance map image, $I_{DM}$, is computed at step 42 with the same dimensions as the input mask image, where $I_{DM}(v)$ is the minimum distance from v to $v_b$ such that $R_m(v_b)=0$. The distance is computed in millimeters using the physical voxel sizes from the CT image 12, as shown in FIG. 9D. Gaussian smoothing is then applied at step 44 to the Euclidean distance map image, $I_{DM}$, with a kernel equal to the CT slice thickness to generate a smoothed distance map 46, $I_{SD}$.

Figure 5:
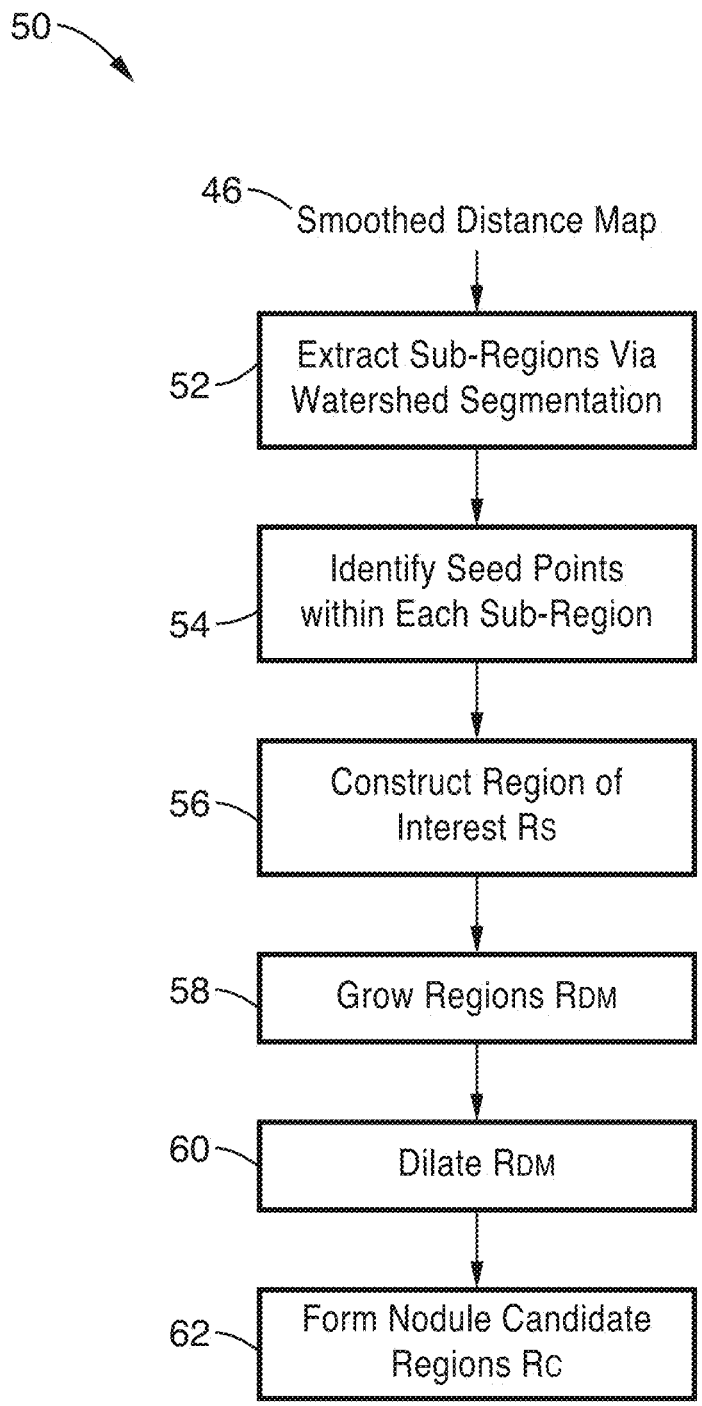
FIG. 5 is a detailed flow diagram of the distance map segmentation step of FIG. 1

FIG. 5 is a detailed flow diagram of the distance map segmentation step 50. First, watershed segmentation is applied at step 52 to the smoothed distance map image 46, $I_{SD}$, to extract contiguous sub-regions around local maxima. Typically watershed segmentation identifies regions around local minima, therefore $I_{SD}$ is inverted prior to computing the watershed. An exemplary nodule/vessel configuration 100 is shown schematically in FIG. 8A. An exemplary watershed segmentation output is shown in FIG. 9E, wherein the distance values increase from lighter shades to darker (non-black) shades.

The voxel with maximum distance map value $I_{DM}(s)$ within each watershed region from step 52 is identified in step 54 as a seed point 102, s. This is illustrated schematically in FIG. 8B. A 60 mm cubic region of interest 104, $R_s$, is then constructed at step 56, centered on s. Step 56 is illustrated schematically in FIG. 8C. It will be appreciated that the size of $R_s$ 104 is a function of typical nodule morphometry, and may be varied accordingly.

From each seed point 102, s, region growing is performed at step 58 to include contiguous voxels that are within $R_s$ having $I_{DM}$ values that are within a percentage threshold range, $p_{DM}$ (0.0 to 1.0), of $I_{DM}(s)$. i.e., a contiguous voxel, v, with distance map value $I_{DM}(v)$ is added to the region if:

$$I_{DM}(s)(1-p_{DM}) \leq I_{DM}(v) \leq I_{DM}(s)(1+p_{DM}). \quad \text{Eq. 2}$$

The region-growing result 106a ($R_{DM}$) is shown schematically in FIG. 8D.

Since the region growing stops when the distance map value goes below $I_{DM}(s)(1-p_{DM})$, $R_{DM}$ will generally not extend to the boundary 100 of the nodule. Therefore, dilation of grown region 106a ($R_{DM}$) is performed at step 60 with a structuring element of half-width=$I_{DM}(s)(1-p_{DM})$ to form dilated region 106b ($R_{DIL}$). Dilated region 106b ($R_{DIL}$) is illustrated schematically in FIG. 8E.

Finally at step 62, a nodule candidate region, $R_C$, is formed by computing $R_{DIL} \cap R_m$, then including voxels contiguous with seed point 102 (s).

Figure 9A:
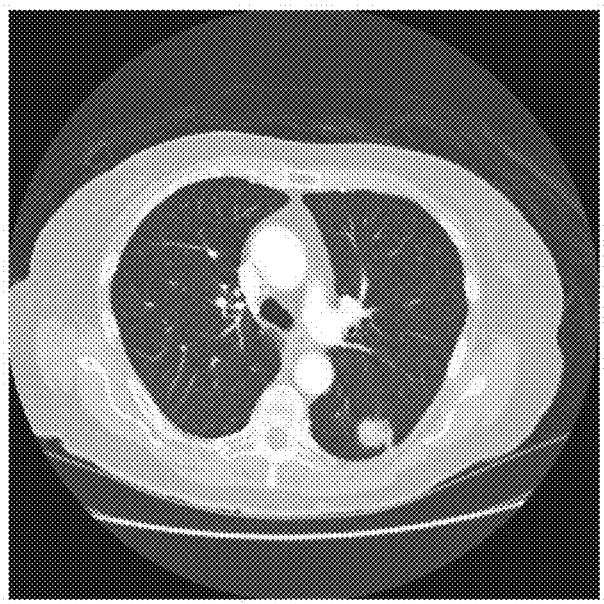
FIG. 9A through FIG. 9G show axial images of 3D surface lung nodule detection and segmentation in accordance with the present invention.
Figure 9B:
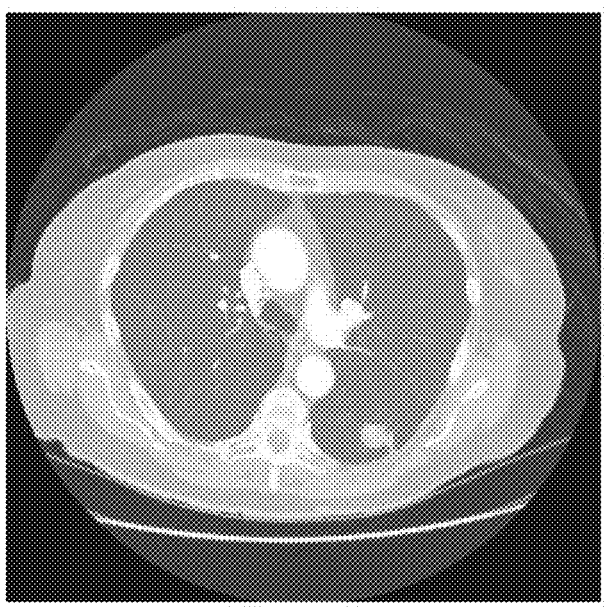
Figure 9C:
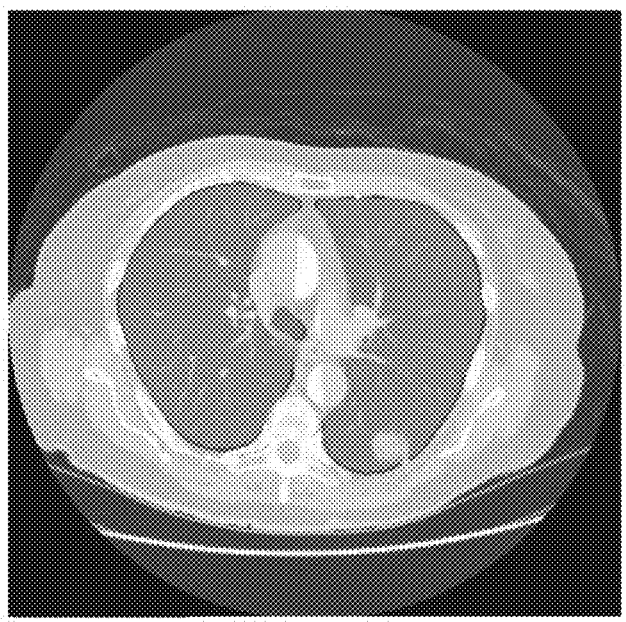
Figure 9D:
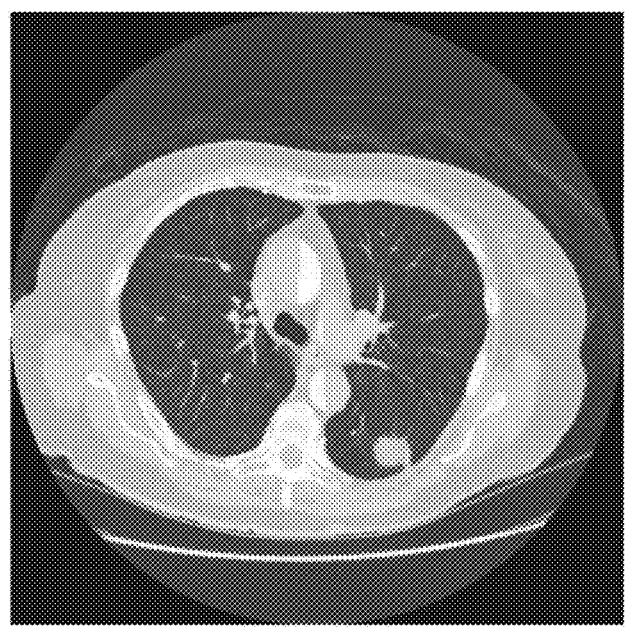
Figure 9E:
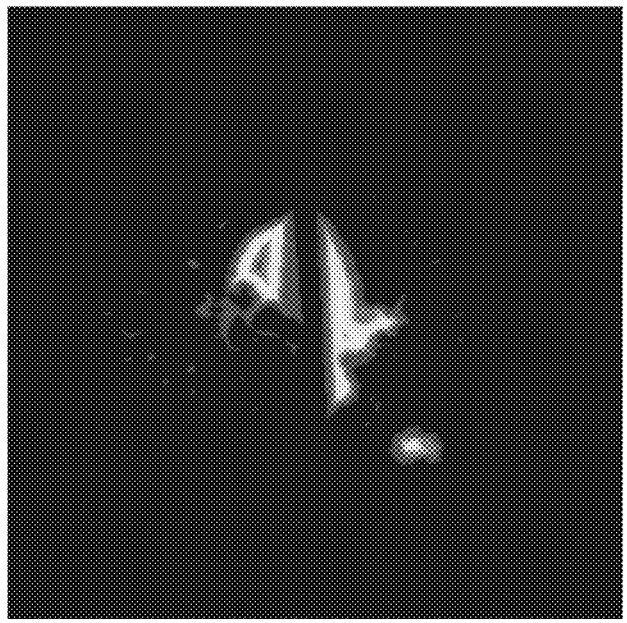
Figure 9F:
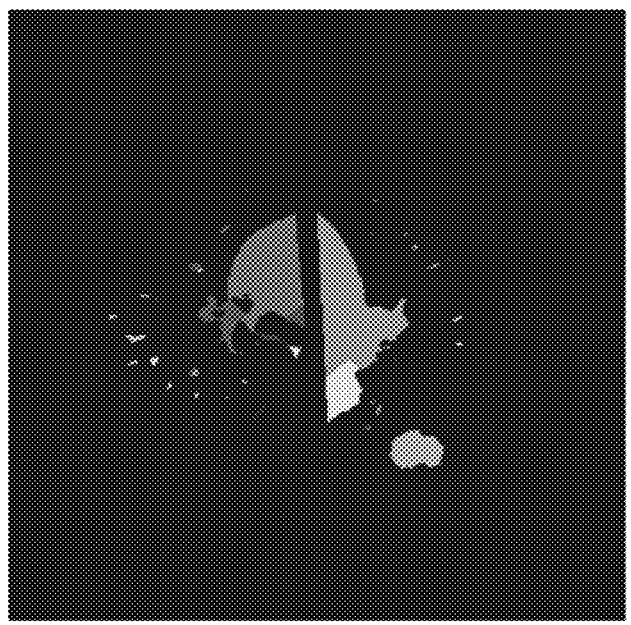

FIG. 9F shows an image of an exemplary watershed segmentation of a distance map of candidates, with each shade representing a separate contiguous watershed region, each having its own seed point.

Figure 6:
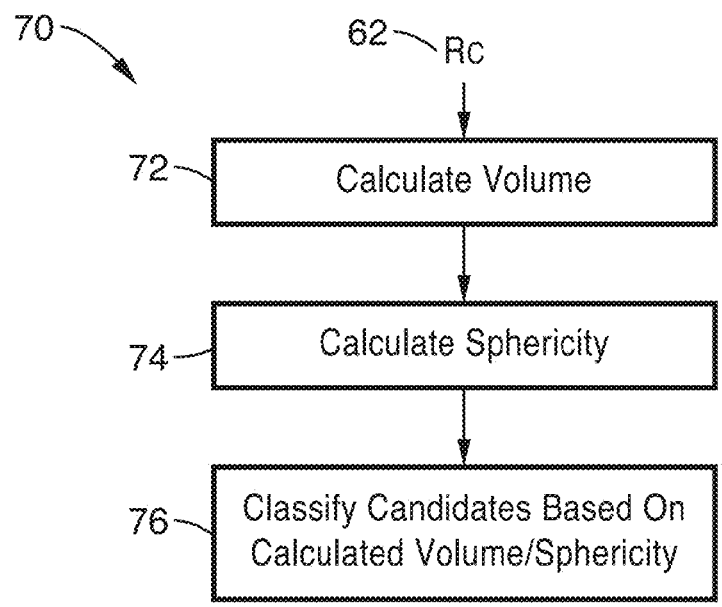
FIG. 6 is a detailed flow diagram of the candidate classification step of FIG. 1.

FIG. 6 is a detailed flow diagram of the candidate classification step 70. The segmented regions (candidates) 62, $R_C$, from step 60 are detected as nodules if they are both large enough and approximately spherical in shape, in contrast to blood vessels which are more tubular. First, the volume of each candidate 62 is calculated at step 72. The sphericity is then calculated at step 74. At step 76, candidates are classified based on the calculated volume and sphericity.

Candidates 62, $R_C$, are classified in step 76 as a "nodule" if they satisfy the following constraints (and "non-nodule" otherwise):

1) Largest area of candidate region 62 ($R_C$) on any 2D slice (in mm$^2$) is greater than $\pi r^2$, where r=0.5*max (4, twice the image slice thickness).

2) Volume of candidate 62 ($R_C$) is between 8 mm$^3$ and 40 cm$^3$. Note, these numbers may be varied according to desired size sensitivity.

3) Sphericity exceeds predetermined minimum threshold $T_s$, where sphericity is calculated as the ratio of the volume of candidate $R_C$ to the volume of the minimum sphere centered on the centroid of $R_C$ that encloses $R_C$.

Figure 9G:
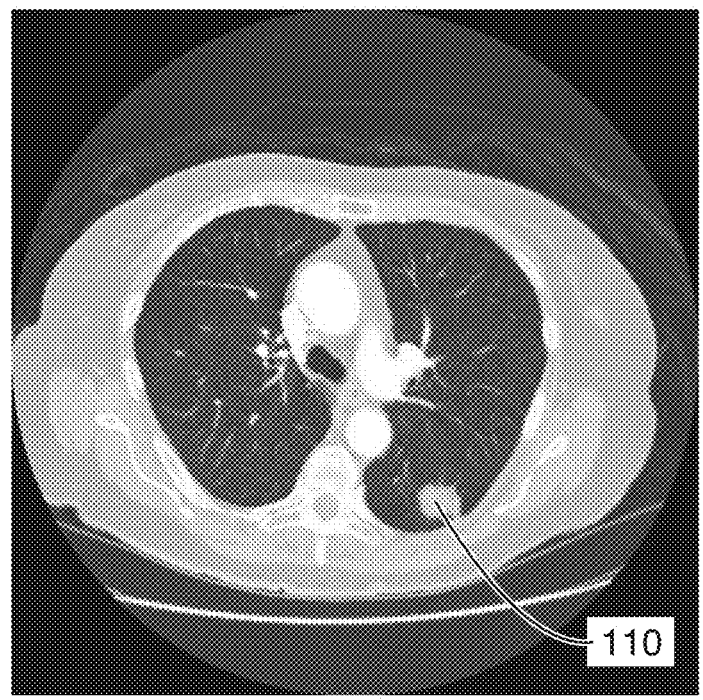

FIG. 9G shows an image of a detected nodule 110 satisfying the criteria above for step 76.

Referring back to FIG. 1, detected solid nodules 80 are based on intensity thresholding values $T=T_{solid}$ that are applied in step 30. An exemplary value for $T_{solid}$ is −300 HU.

Steps 20 through 70 may also be are repeated with a lower threshold, $T_{ggo}$, to detect ground glass nodule regions 82. An exemplary value for $T_{ggo}$ is −700 HU. Ground glass nodule regions 82 are rejected if they overlap with a solid nodule region. The remaining ground glass nodules may then be combined with the set of solid nodules to generate a final set of nodule regions.

Figure 7:
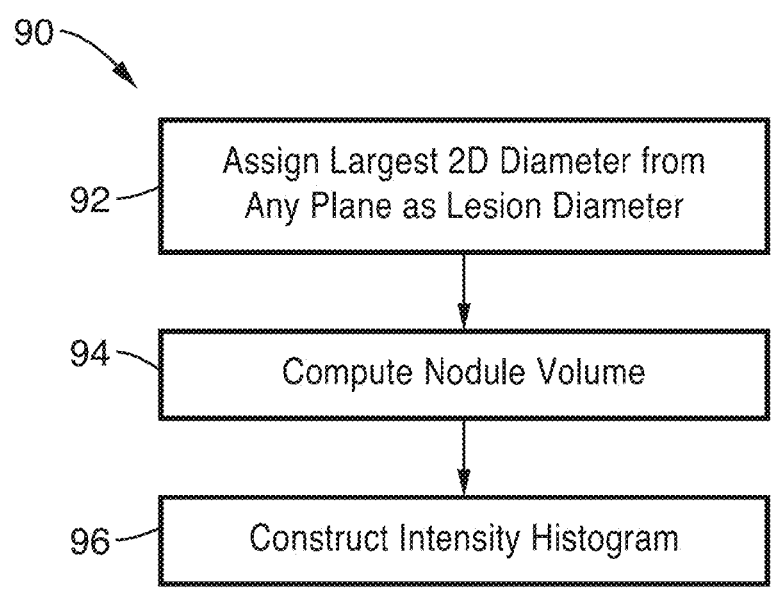
FIG. 7 is a detailed flow diagram of the quantitative analysis step of FIG. 1.

Quantitative analysis may also be preformed on the obtained set of nodules 80/82. FIG. 7 is a detailed flow diagram of an exemplary quantitative analysis step 90.

At step 92, a lesion diameter may be computed. For a given plane (typically axial, sagittal, or coronal), the 3D nodule ROI 80/82 is divided into a set of 2D ROIs. For each 2D ROI a set of boundary points is extracted. The distance between each pair of boundary points is then computed and the maximum distance is selected as the largest 2D diameter. The largest of the 2D diameters from any plane is selected as the lesion diameter At step 94, the volume of a nodule 80/82 is computed by summing the physical volumes of each voxel included in the nodule ROI.

At step 96, an intensity histogram may also be constructed for each nodule 80/82 using the intensity values from the original CT image 12 within the nodule's ROI. Descriptive statistics of the histogram may then be derived.

Referring back to FIG. 1, the detected nodules 80/82 may then be displayed in step 100 as overlays on the original image 12, along with measurements for each nodule 80/82 derived in quantitative analysis step 90.

FIG. 9A through FIG. 9G show images of an exemplary 3D surface lung nodule detection and segmentation in accordance with the present invention. FIG. 9A illustrates an original chest CT image. FIG. 9B illustrates an exemplary output of the lung segmentation method of the present invention. FIG. 9C is an image of convex hull of lung region. FIG. 9D is an exemplary image of the intensity thresholding segmentation method of the present invention. FIG. 9E shows an image of an exemplary distance map of segmented region (with distance values increasing from blue to red). FIG. 9F shows an image of an exemplary watershed segmentation of a distance map (with each shade representing a separate contiguous region). FIG. 9G shows an image of a final detected and segmented nodule 110 using region growing from each seed provided by the watershed and classification based on size and shape features.

Figure 10:
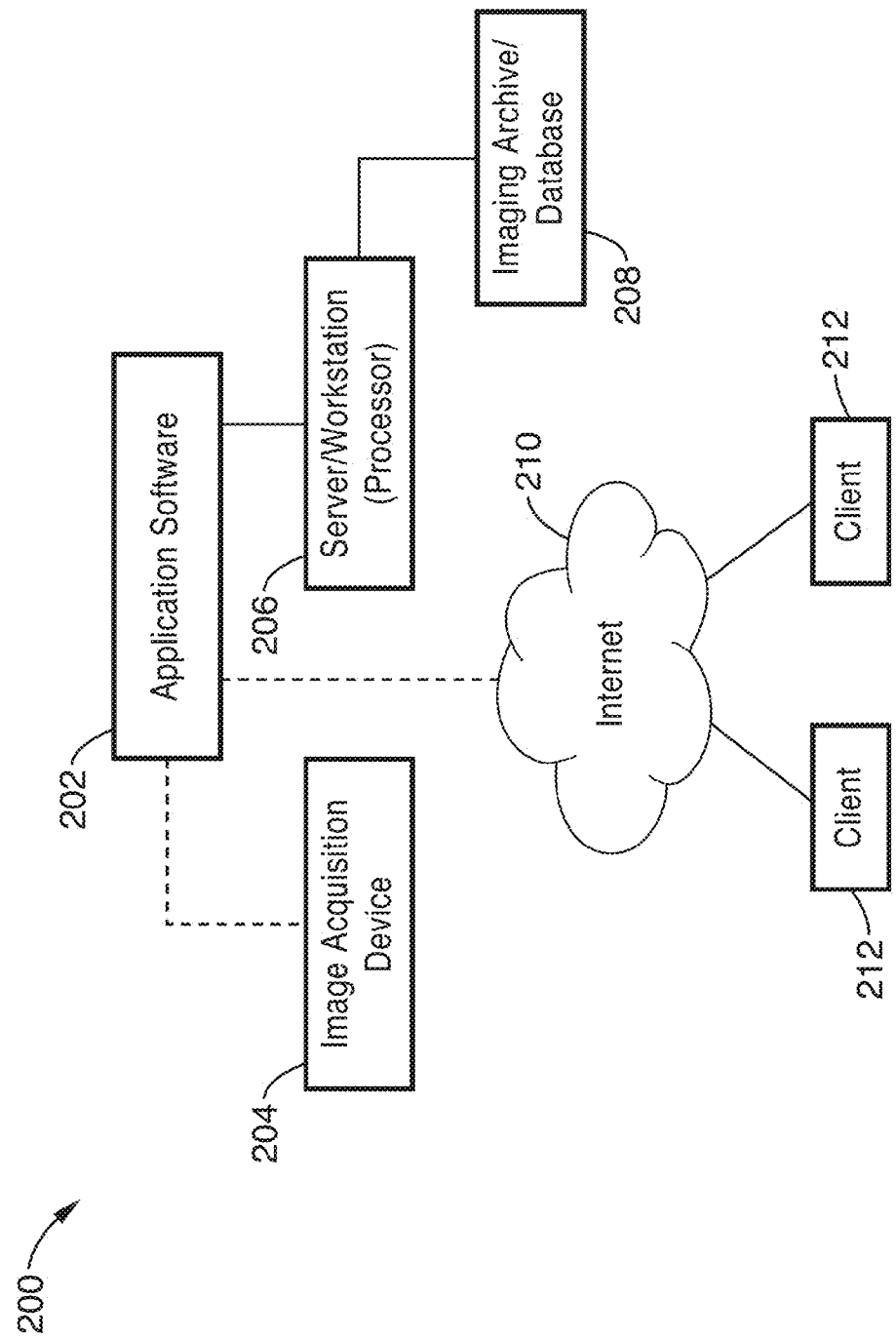
FIG. 10 is a schematic diagram of a lung nodule detection system of the present invention.

FIG. 10 is a schematic diagram of a lung nodule detection system 200 of the present invention, wherein one or more steps or methods identified in FIGS. 1 through FIG. 8E are implemented as computer application software 202. In one embodiment, application software 202 may be run on a processor such as an individual medical imaging workstation 206, e.g. either at the image acquisition device (CT scanner) 204, or on a reading workstation. The application software 202 may also be run on a centralized server 206 or cluster of servers in a radiology department or medical center. Running on a server 206 may offer some advantages in terms of interfacing with a centralized imaging archive and storing reports in a centralized database 208. The system 200 may also be accessed remotely (via the Internet 210), for example, using GRID computing. Using this approach, the system 200 is made available as a GRID service and clients 212 with proper authentication/authorization can access it world-wide.

Accordingly, the systems and methods of the present invention provide a powerful automation combined with intuitive, human intervention and feedback to achieve a robust, widely-applicable system that can even handle the most diseased or abnormal images where fully automated segmentation is not possible. The automated pre-processing of data performed by the method 10 of the present invention is of significant importance, since manual segmentation of large numbers of scans would be impractical.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A method for automatic detection of lung nodules, comprising: inputting data from a computed tomography (CT) image; segmenting the image to acquire one or more lung regions; intensity thresholding the one or more lung regions to generate a mask region comprising one or more high-intensity regions corresponding to anatomical structures within the one or more lung regions; computing a Euclidean distance map of the mask region; performing watershed segmentation of the Euclidean distance map to generate one or more sub-regions; identifying a seed point for each sub region of the one or more sub-regions; growing one or more candidate regions from the seed point of each sub-region; and classifying one or more candidate regions as a lung nodule based on one or more geometric features of the one or more candidate regions.

2. A method as recited in any of the previous embodiments, wherein segmenting the image comprises: segmenting a chest wall region of the image by intensity thresholding bright voxels in the CT image and selecting the largest connected 3D component; and segmenting a lung region from the chest wall region by intensity thresholding dark voxels in the CT image and selecting the largest connected 3D component.

3. A method as recited in any of the previous embodiments, wherein segmenting the image further comprises: computing the convex hull of the segmented lung region.

4. A method as recited in any of the previous embodiments, wherein intensity thresholding the one or more lung regions is performed at a first threshold value for detection of solid nodule candidate regions.

5. A method as recited in any of the previous embodiments, wherein intensity thresholding the one or more lung regions is performed at a second threshold value for detection of ground glass nodule candidate regions.

6. A method as recited in any of the previous embodiments, wherein Gaussian smoothing is applied to the Euclidean distance map prior to watershed segmentation.

7. A method as recited in any of the previous embodiments, wherein the one or more sub-regions generated from watershed segmentation are contiguous with local maxima in the Euclidean distance map.

8. A method as recited in any of the previous embodiments, wherein identifying a seed point for each sub region comprises indentifying a voxel having a maximum Euclidean distance map value within each sub-region as the seed corresponding to the sub-region.

9. A method as recited in any of the previous embodiments, wherein growing one or more candidate regions comprises: generating a cubic region of interest centered around each seed point; and including continuous voxels within the region of interest as voxels in a candidate region; the included voxels having Euclidean distance map values falling within a predetermined threshold range.

10. A method as recited in any of the previous embodiments, further comprising: dilating each of the one or more grown candidate regions.

11. A method as recited in any of the previous embodiments, wherein classifying one or more candidate regions comprises: calculating a volume of a candidate region; and identifying a candidate region as a nodule as a function of the calculated volume falling within a threshold range.

12. A method as recited in any of the previous embodiments, wherein classifying one or more candidate regions further comprises: calculating a sphericity of a candidate region; wherein the sphericity is calculated as a ratio of the calculated volume of a candidate region to a volume of a minimum sphere centered about a centroid of the candidate volume, and identifying a candidate region as a nodule as a function of the calculated sphericity exceeding a threshold value.

13. A method as recited in any of the previous embodiments, further comprising: calculating a volume of an identified lung nodule by summing volumes of each voxel in an identified nodule.

14. A method as recited in any of the previous embodiments, further comprising: calculating a diameter of an identified lung nodule.

15. A method as recited in any of the previous embodiments, wherein the diameter is calculated by: dividing the lung nodule into a plurality of 2D regions of interest in one or more planes; extracting boundary points for each 2D region of interest; and identifying a maximum diameter from the boundary points in each 2D region of interest; identifying a largest maximum diameter from each of the planes as the nodule diameter.

16. A method as recited in any of the previous embodiments, further comprising: overlaying an image of the identified lung nodule over the CT image.

17. A system for automatically segmenting a computed tomography (CT) image of a patient's lung, comprising: a processor; programming executable on the processor and configured for: inputting data from the CT image; segmenting the image to acquire one or more lung regions; intensity thresholding the one or more lung regions to generate a mask region comprising one or more high-intensity regions corresponding to anatomical structures within the one or more lung regions; computing a Euclidean distance map of the mask region; performing watershed segmentation of the Euclidean distance map to generate one or more sub-regions; identifying a seed point for each sub region of the one or more sub-regions; growing one or more candidate regions from the seed point of each sub-region; and classifying one or more candidate regions as a lung nodule based on one or more geometric features of the one or more candidate regions.

18. A system as recited in any of the previous embodiments, wherein segmenting the image comprises: segmenting a chest wall region of the image by intensity thresholding bright voxels in the CT image and selecting the largest connected 3D component; and segmenting a lung region from the chest wall region by intensity thresholding dark voxels in the CT image and selecting the largest connected 3D component.

19. A system as recited in any of the previous embodiments, wherein segmenting the image further comprises: computing the convex hull of the segmented lung region.

20. A system as recited in any of the previous embodiments, wherein intensity thresholding the one or more lung regions is performed at a first threshold value for detection of solid nodule candidate regions.

21. A system as recited in any of the previous embodiments, wherein intensity thresholding the one or more lung regions is performed at a second threshold value for detection of ground glass nodule candidate regions.

22. A system as recited in any of the previous embodiments, wherein Gaussian smoothing is applied to the Euclidean distance map prior to watershed segmentation.

23. A system as recited in any of the previous embodiments, wherein the one or more sub-regions generated from watershed segmentation are contiguous with local maxima in the Euclidean distance map.

24. A system as recited in any of the previous embodiments, wherein identifying a seed point for each sub region comprises indentifying a voxel having a maximum Euclidean distance map value of each sub-region as the seed corresponding to the sub-region.

25. A system as recited in any of the previous embodiments, wherein growing one or more candidate regions comprises: generating a cubic region of interest centered around each seed point; and including continuous voxels within the region of interest as voxels in a candidate region; the included voxels having Euclidean distance map values falling within a predetermined threshold range.

26. A system as recited in any of the previous embodiments, further comprising: dilating each of the one or more grown candidate regions.

27. A system as recited in any of the previous embodiments, wherein classifying one or more candidate regions comprises: calculating a volume of a candidate region; and identifying a candidate region as a nodule as a function of the calculated volume falling within a threshold range.

28. A system as recited in any of the previous embodiments, wherein classifying one or more candidate regions further comprises: calculating a sphericity of a candidate region; wherein the sphericity is calculated as a ratio of the calculated volume of a candidate region to a volume of a minimum sphere centered about a centroid of the candidate volume, and identifying a candidate region as a nodule as a function of the calculated sphericity exceeding a threshold value.

29. A system as recited in any of the previous embodiments, further comprising: calculating a volume of an identified lung nodule by summing volumes of each voxel in an identified nodule.

30. A system as recited in any of the previous embodiments, further comprising: calculating a diameter of an identified lung nodule.

31. A system as recited in any of the previous embodiments, wherein the diameter is calculated by: dividing the lung nodule into a plurality of 2D regions of interest in one or more planes; extracting boundary points for each 2D region of interest; identifying a maximum diameter from the boundary points in each 2D region of interest; and identifying a largest maximum diameter from each of the planes as the nodule diameter.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method for automatic detection of lung nodules, comprising:
    inputting data from a computed tomography (CT) image;
    segmenting the image to acquire one or more lung regions;
    intensity thresholding the one or more lung regions to generate a mask region comprising one or more high-intensity regions corresponding to anatomical structures within the one or more lung regions;
    computing a Euclidean distance map of the mask region;
    performing watershed segmentation of the Euclidean distance map to generate one or more sub-regions;
    identifying a seed point for each sub region of the one or more sub-regions;
    growing one or more candidate regions from the seed point of each sub-region; and
    classifying one or more candidate regions as a lung nodule based on one or more geometric features of the one or more candidate regions.

2. A method as recited in claim 1, wherein segmenting the image comprises:
    segmenting a chest wall region of the image by intensity thresholding bright voxels in the CT image and selecting the largest connected 3D component; and
    segmenting a lung region from the chest wall region by intensity thresholding dark voxels in the CT image and selecting the largest connected 3D component.

3. A method as recited in claim 2, wherein segmenting the image further comprises computing the convex hull of the segmented lung region.

4. A method as recited in claim 1, wherein intensity thresholding the one or more lung regions is performed at a first threshold value for detection of solid nodule candidate regions.

5. A method as recited in claim 1, wherein intensity thresholding the one or more lung regions is performed at a second threshold value for detection of ground glass nodule candidate regions.

6. A method as recited in claim 1, wherein Gaussian smoothing is applied to the Euclidean distance map prior to watershed segmentation.

7. A method as recited in claim 1, wherein the one or more sub-regions generated from watershed segmentation are contiguous with local maxima in the Euclidean distance map.

8. A method as recited in claim 7, wherein identifying a seed point for each sub-region comprises identifying a voxel having a maximum Euclidean distance map value within each sub-region as the seed corresponding to the sub-region.

9. A method as recited in claim 8, wherein growing one or more candidate regions comprises:
generating a cubic region of interest centered around each seed point; and
including continuous voxels within the region of interest as voxels in a candidate region;
the included voxels having Euclidean distance map values falling within a predetermined threshold range.

10. A method as recited in claim 9, further comprising dilating each of the one or more grown candidate regions.

11. A method as recited in claim 1, wherein classifying one or more candidate regions comprises:
calculating a volume of the candidate region; and
identifying the candidate region as a nodule as a function of the calculated volume falling within a threshold range.

12. A method as recited in claim 11, wherein classifying one or more candidate regions further comprises:
calculating a sphericity of the candidate region;
wherein the sphericity is calculated as a ratio of the calculated volume of the candidate region to a volume of a minimum sphere centered about a centroid of the candidate volume, and
identifying the candidate region as a nodule as a function of the calculated sphericity exceeding a threshold value.

13. A method as recited in claim 1, further comprising calculating a volume of an identified lung nodule by summing volumes of each voxel in the identified lung nodule.

14. A method as recited in claim 1, further comprising calculating a diameter of an identified lung nodule.

15. A method as recited in claim 14, wherein the diameter is calculated by:
dividing the lung nodule into a plurality of 2D regions of interest in one or more planes;
extracting boundary points for each 2D region of interest;
identifying a maximum diameter from the boundary points in each 2D region of interest; and
identifying a largest maximum diameter from each of the planes as the nodule diameter.

16. A method as recited in claim 1, further comprising overlaying an image of the identified lung nodule over the CT image.

17. A system for automatically segmenting a computed tomography (CT) image of a patient's lung, comprising:
a processor;
programming executable on the processor and configured for:
inputting data from the CT image;
segmenting the image to acquire one or more lung regions;
intensity thresholding the one or more lung regions to generate a mask region comprising one or more high-intensity regions corresponding to anatomical structures within the one or more lung regions;
computing a Euclidean distance map of the mask region;
performing watershed segmentation of the Euclidean distance map to generate one or more sub-regions;
identifying a seed point for each sub region of the one or more sub-regions;
growing one or more candidate regions from the seed point of each sub-region; and
classifying one or more candidate regions as a lung nodule based on one or more geometric features of the one or more candidate regions.

18. A system as recited in claim 17, wherein segmenting the image comprises:
segmenting a chest wall region of the image by intensity thresholding bright voxels in the CT image and selecting the largest connected 3D component; and
segmenting a lung region from the chest wall region by intensity thresholding dark voxels in the CT image and selecting the largest connected 3D component.

19. A system as recited in claim 18, wherein segmenting the image further comprises computing the convex hull of the segmented lung region.

20. A system as recited in claim 17, wherein intensity thresholding the one or more lung regions is performed at a first threshold value for detection of solid nodule candidate regions.

21. A system as recited in claim 17, wherein intensity thresholding the one or more lung regions is performed at a second threshold value for detection of ground glass nodule candidate regions.

22. A system as recited in claim 17, wherein Gaussian smoothing is applied to the Euclidean distance map prior to watershed segmentation.

23. A system as recited in claim 17, wherein the one or more sub-regions generated from watershed segmentation are contiguous with local maxima in the Euclidean distance map.

24. A system as recited in claim 23, wherein identifying a seed point for each sub region comprises indentifying a voxel having a maximum Euclidean distance map value of each sub-region as the seed corresponding to the sub-region.

25. A system as recited in claim 24, wherein growing one or more candidate regions comprises:
generating a cubic region of interest centered around each seed point; and
including continuous voxels within the region of interest as voxels in a candidate region;
the included voxels having Euclidean distance map values falling within a predetermined threshold range.

26. A system as recited in claim 25, further comprising:
dilating each of the one or more grown candidate regions.

27. A system as recited in claim 17, wherein classifying one or more candidate regions comprises:
calculating a volume of the candidate region; and
identifying a candidate region as a nodule as a function of the calculated volume falling within a threshold range.

28. A system as recited in claim 27, wherein classifying one or more candidate regions further comprises:
calculating a sphericity of a candidate region;
wherein the sphericity is calculated as a ratio of the calculated volume of a candidate region to a volume of a minimum sphere centered about a centroid of the candidate volume, and
identifying a candidate region as a nodule as a function of the calculated sphericity exceeding a threshold value.

29. A system as recited in claim 27, further comprising:
calculating a volume of an identified lung nodule by summing volumes of each voxel in the identified lung nodule.

30. A system as recited in claim 17, further comprising calculating a diameter of an identified lung nodule.

31. A system as recited in claim 30, wherein the diameter is calculated by:
dividing the lung nodule into a plurality of 2D regions of interest in one or more planes;
extracting boundary points for each 2D region of interest;
identifying a maximum diameter from the boundary points in each 2D region of interest; and
identifying a largest maximum diameter from each of the planes as the nodule diameter.

32. A system as recited in claim 17, further comprising overlaying an image of the identified lung nodule over the CT image.

* * * * *